United States Patent [19]

Sirkkola et al.

[11] 4,425,786

[45] Jan. 17, 1984

[54] METHOD AND APPARATUS FOR IMPACT TESTING OF BEND SPECIMEN

[75] Inventors: Erkki Sirkkola, Kirkkonummi; Heikki Kotilainen, Espoo, both of Finland

[73] Assignee: Valtion Teknillinen Tutkimuslaitos, Espoo, Finland

[21] Appl. No.: 194,132

[22] Filed: Oct. 6, 1980

[30] Foreign Application Priority Data

Oct. 10, 1979 [FI] Finland .................................. 793151

[51] Int. Cl.³ .............................................. G01N 3/30
[52] U.S. Cl. ....................................................... 73/12
[58] Field of Search ................. 73/844, 799, 849, 850, 73/851, 852, 853, 12

[56] References Cited

U.S. PATENT DOCUMENTS

| | | | |
|---|---|---|---|
| 2,188,898 | 2/1940 | Haskell et al. | 73/844 |
| 2,359,044 | 9/1944 | MacBride | 73/844 |
| 2,362,589 | 11/1944 | Simmons, Jr. | 73/12 |
| 2,450,662 | 11/1948 | Hofmann | 73/844 |
| 3,285,060 | 11/1966 | Pessen | 73/844 |
| 4,347,735 | 9/1982 | Desai et al. | 73/849 X |

FOREIGN PATENT DOCUMENTS

| | | | |
|---|---|---|---|
| 1150224 | 12/1960 | Fed. Rep. of Germany | 73/12 |
| 634171 | 11/1978 | U.S.S.R. | 73/12 |
| 735959 | 5/1980 | U.S.S.R. | 73/851 |

OTHER PUBLICATIONS

Mohsenin, How Much Can an Apple Take; 1965, Instrumentation 1st Quarter, vol. 18 #1.
Greenbank, L. R. et al. (of New Zeland) Apparatus for Bending Crystals at Constant Strain Rate, J. Phys. E (G.B.) vol. 3, Nov. 1970, p. 949.
Testing Machines Inc. National Force and Ordance Company, Sales Brochure; Jun. 1960.

Primary Examiner—Anthony V. Ciarlante
Attorney, Agent, or Firm—Martin Smolowitz

[57] ABSTRACT

A method and apparatus for testing of impact toughness of a bend specimen having a notch or similar in a middle portion thereof. According to the invention the bend specimen is supported by a rigid support in a middle area at the opposite side of the specimen with respect to the notch, and is hit from the notched side at two points, positioned on each side of the middle area, with a hammer comprising two spaced-apart hitting edges. The hammer may be of pendulum type and mounted for pivotal movement around a horizontal axis positioned above said specimen.

8 Claims, 5 Drawing Figures

(A-A)

METHOD AND APPARATUS FOR IMPACT TESTING OF BEND SPECIMEN

BACKGROUND OF THE INVENTION

1. Field of the Invention

This invention concerns a method and an apparatus for impact testing of bend specimens, and which reduce the inertial load effects in an impact test and also change the state of stress in the test specimen towards 3-point bending and therefore enable more reliable analysis of the data.

2. Description of the Prior Art

The impact test is generally used to measure the toughness of materials and the methods and the test specimens are standardized in most countries (ASTM E 370, DIN 51222). It is also a general practice to measure and to record the force which is acting on the specimen during the impact (Turner, E.C.: "Measurement of Fracture Toughness by Instrumented Impact Test", Impact Testing of Metals, ASTM STP 466, American Society for Testing and Materials, 1970, pp. 93–114; Instrumented Impact Testing, ASTM STP 563, American Society for Testing and Materials, 1974).

The impact test result is often presented in the form of a force-time or a force-displacement diagram. It is also general knowledge that when the hammer first hits the specimen, a significant force is observed because the mass of the specimen has to be accelerated to the speed of the hammer. This force is inevitable and it will occur even when the specimen is only supported and is free to fly away. It has been observed that the inertial load alone can break a brittle specimen (Radon, J.C. and Turner, C.E.: "Fracture Toughness Measurements by Instrumented Impact Test", Engng. Fracture Mech. Vol. 1, pp. 411–428, 1969).

This inertial force peak sets the specimen and the load transducer to a very rapid vibration and therefore the force measured from the instrumented tup bears no actual resemblance to the real force which is acting on the specimen during approximately the first 20 or 30 microseconds. Brittle specimens very often break during this initial period and in this case the inertial load effects completely mask the true breaking load and the true energy consumed in the fracture process (the consumed energy is usually calculated by integrating the area under the force-displacement diagram and it is almost impossible to separate the fracture energy from the energy consumed only for acceleration of the specimen).

The significance and the effects of the inertial load are presented in Saxton, H.J., Ireland, D.R. and Server, W.L.: "Analysis and Control of Inertial Effects During Instrumented Impact Testing," ASTM STP 563, American Society for Testing and Materials, 1974, pp. 50–73.

The vibrations produced by the inertial load are presented in FIG. 1, which also gives schematic presentation of the events in the beginning of the impact.

At the moment marked 0, the tup touches the specimen and starts to accelerate it. At the moment 1 the midsection of the specimen has reached the speed of the hammer and the force reaches its first peak. Because the specimen and the tup are compressed during the acceleration, the specimen tries to fly off and the force diminishes after the moment 1. At the same time, the specimen starts to bend and the reaction forces start to appear at the supports. The bending of the specimen consumes rapidly the extra kinetic energy of the specimen and the tup hits the specimen a second time beginning at the moment 2. Because the speed differences are smaller this time, the force generated by the acceleration is smaller. The same process of hitting and getting loose then repeats itself several times with decreasing force-amplitude and the force is summed onto the actual bending force.

A very harmful effect of the inertial load acting on the notched section of the specimen is its suggested interference with the fracture initiation process at the notch root. The high inertial load peak produces a complex stress wave across the notch and according to Seifert et al. (Seifert, K. and Meyer, L. W.: "Möglichkeiten zum Vermindern des Aufschlagimpulses bei Bruchzähigkeitsprüfungen unter schlagartiger Beanspruchung", Materialprüf. 19, Nr. 6, Juni 1977) this effect might cause about 20 percent decrease in the fracture load. The same investigators refer also to unpublished finite-element calculations which predict the same effect. These results may partly explain why correlations between the Charpy-V impact energy and other toughness measurements are relatively poor.

Because it is evident that the force measured from the tup does not give reliable results during the first moments of the impact, several methods have been proposed to avoid inertial load effects. One solution is to measure the bending moment directly from the specimen by instrumenting it with strain gauges. This method is time consuming and expensive and it is not applicable to low or high temperature tests. It has also been proposed to calculate the bending force from the elapsed time before specimen breaks. This indirect method is based on the findings that the bending force indirect method is based on the findings that the bending force depends almost linearly of time. The drawback in this method is that it requires the moment when the specimen breaks to be measured very accurately and this can be done only by instrumenting the specimen. Most widely used method is to reduce the impact speed. The lower speed produces less vibrations and makes the analysis of the force-time diagram easier. On the other hand, one loses some of the dynamic nature of the test. The available energy decreases and therefore also the velocity decreases more during the specimen bending and this may increase the scatter of the test results.

It is also possible to move the inertial load effects away from the tup by attaching the specimen to the moving hammer. This method has been found effective by several investigators. In FIG. 2 is presented an actual force-displacement diagram for aluminum Charpy-V specimen (solid line). The other superimposed diagram (dotted line) in FIG. 2 was gained with same kind of specimen but, this time the specimen was tied onto the hammer. The first inertial peak was avoided and the vibrations also became smaller. The explanation for this is that the inertial load is acting on the two supports and because it is now divided on both of the supports, its magnitude is halved and it also takes time for the diminished vibrations to reach the load measuring tup. This method is the only one which also eliminates the harmful transverse stress wave across the notch and is therefore bound to give more reliable results. Unfortunately it is practically impossible to use this method at any other than room temperature, because the attaching of the specimen is time consuming and even if it were possible to attach a very cold or hot specimens in this way, the temperature of the specimen cannot be known at the moment of the actual impact.

SUMMARY OF THE INVENTION

The present invention for impact toughness testing of bend specimens combines the benefits of the ordinary Charpy test and those of the method of attaching the specimen onto the hammer. This is done by inverting the geometry of the tester in such a way that the stationary specimen is bent round the stationary tup by hitting both ends of the specimen simultaneously with the hammer which has two hitting edges. The specimen is only supported, for example, on a plate and is free to deform in the bending plane. Force can be measured from the tup. According to the present invention, the inertial load effects are mainly acting on the hitting edges and only reduced vibrations are transferred to the middle section of the specimen. It is very important to notice that there exists no inertial load acting across the notch and therefore there exists no extra stress wave in the notched section. It must be underlined that in the published calculations of the stresses at the notch root, the effect of the extra transverse stress wave is not accounted for and therefore the present construction gives a stress state at the notch root which is closer to the one assumed by the general analyzing methods.

It is also possible to modify the tup by designing it to consist of two tips with little spacing between them. This modification would change the test geometry from 3-point bending to 4-point bending. It is also possible to equip the specimen with some kind of a notch opening gauge becsue the mid-section of the specimen remains relatively stationary during the test. The test can be performed of different temperatures as the ordinary Charpy test because it is not necessary to attach the specimen. One must only make sure that the specimen is placed symmetrically and that it is aligned so that the hitting blow meets its both ends simultaneously. The required positioning can be done simply with a positioning device.

DESCRIPTION OF THE PREFERRED EMBODIMENTS

Figure 1:
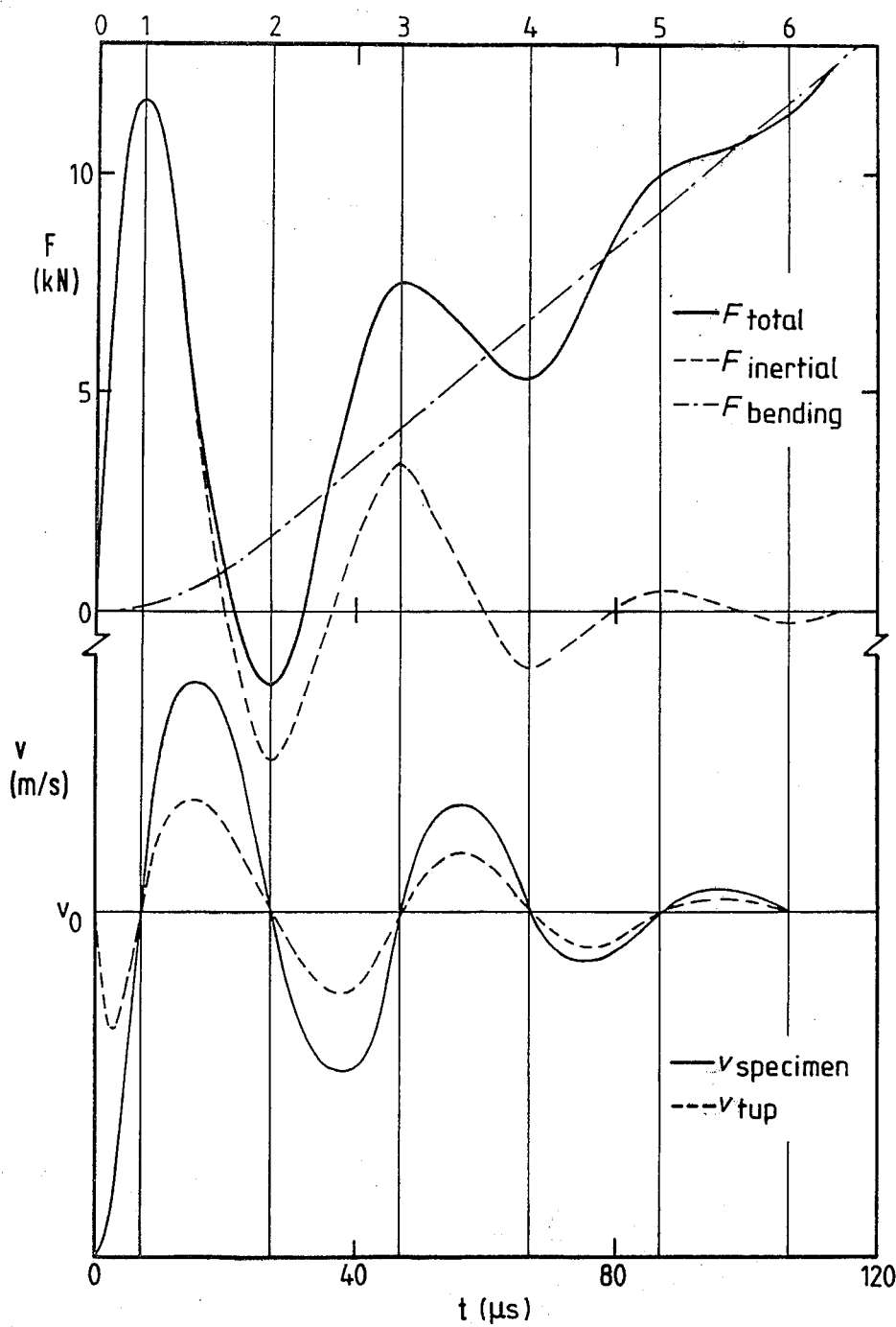
FIG. 1 illustrates the vibrations produced by the inertial load and the events at the beginning of the impact (state of the art)
Figure 2:
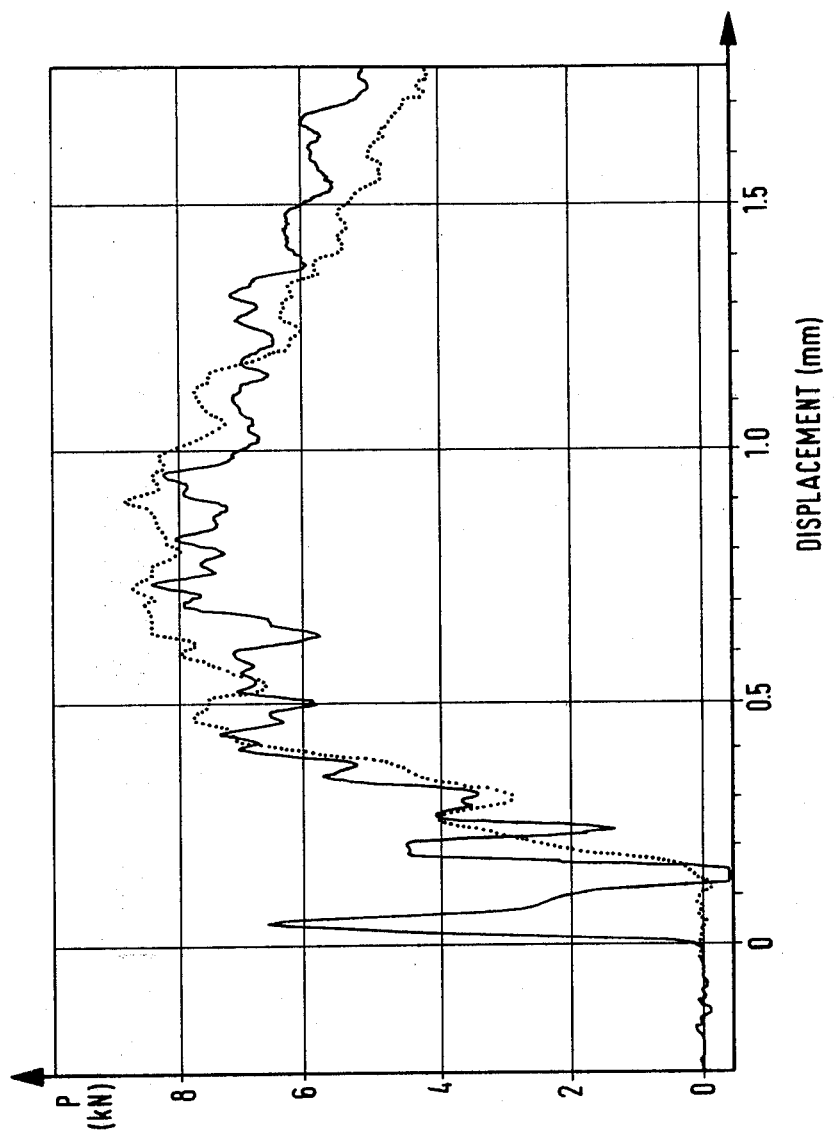
FIG. 2 illustrates a force-displacement diagram for aluminum Charpy-V specimen (solid line) and for specimen tied onto the hammer (dotted line) (state of the art)
Figure 3:
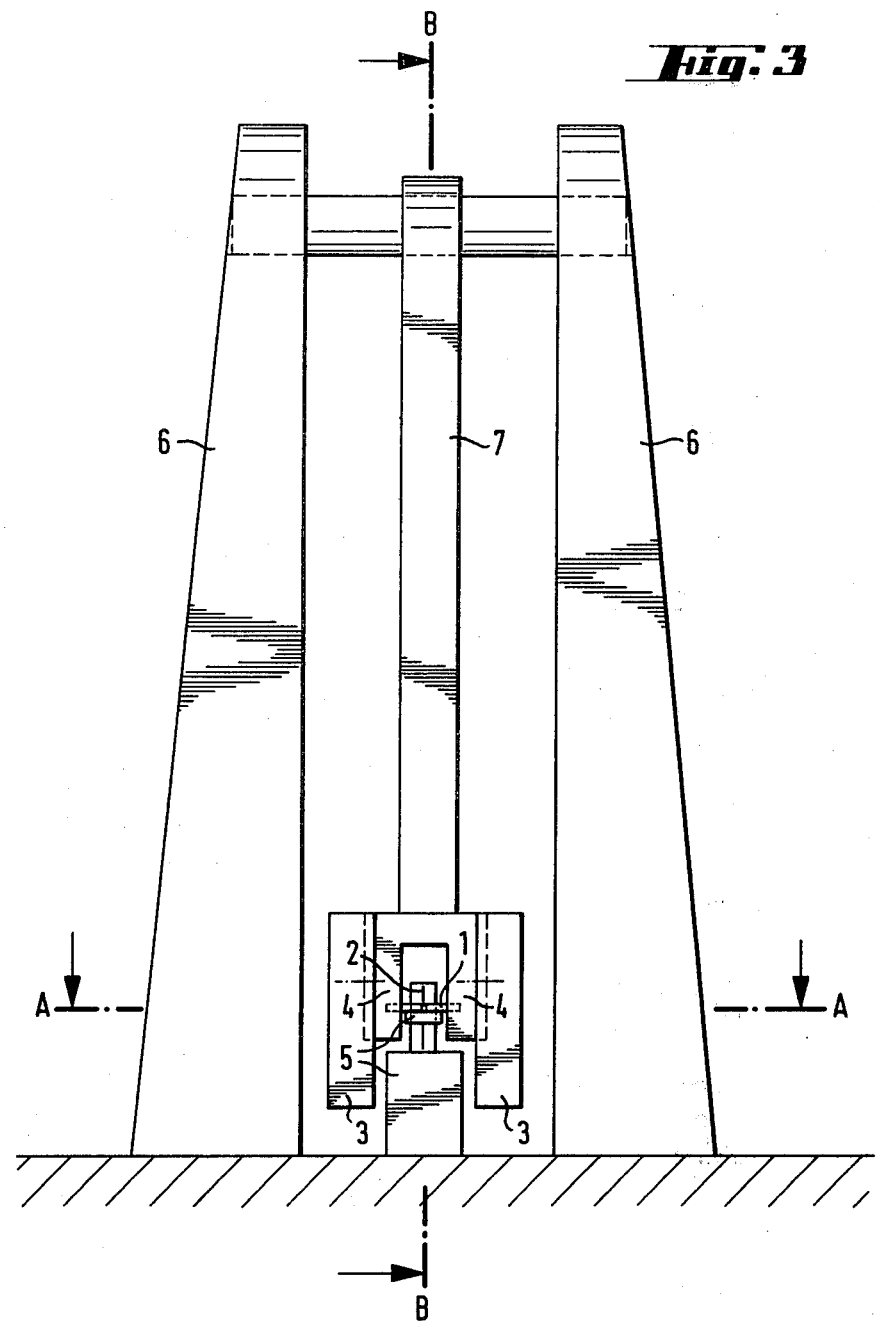
FIG. 3 illustrates a front view of the apparatus according to the present invention.
Figure 4:
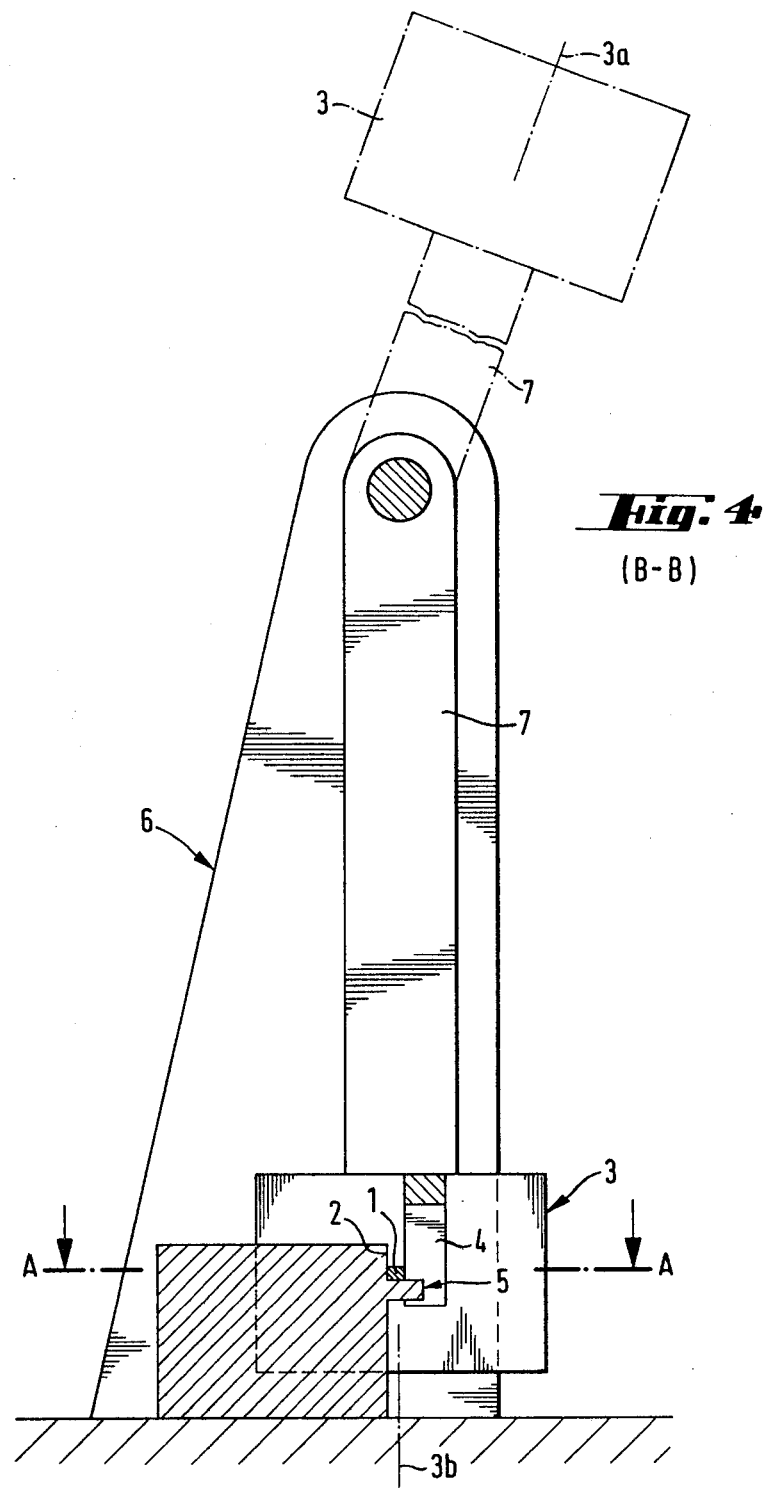
FIG. 4 illustrates a vertical section along line B-B of the same apparatus with the hammer in upper and lower positions.
Figure 5:
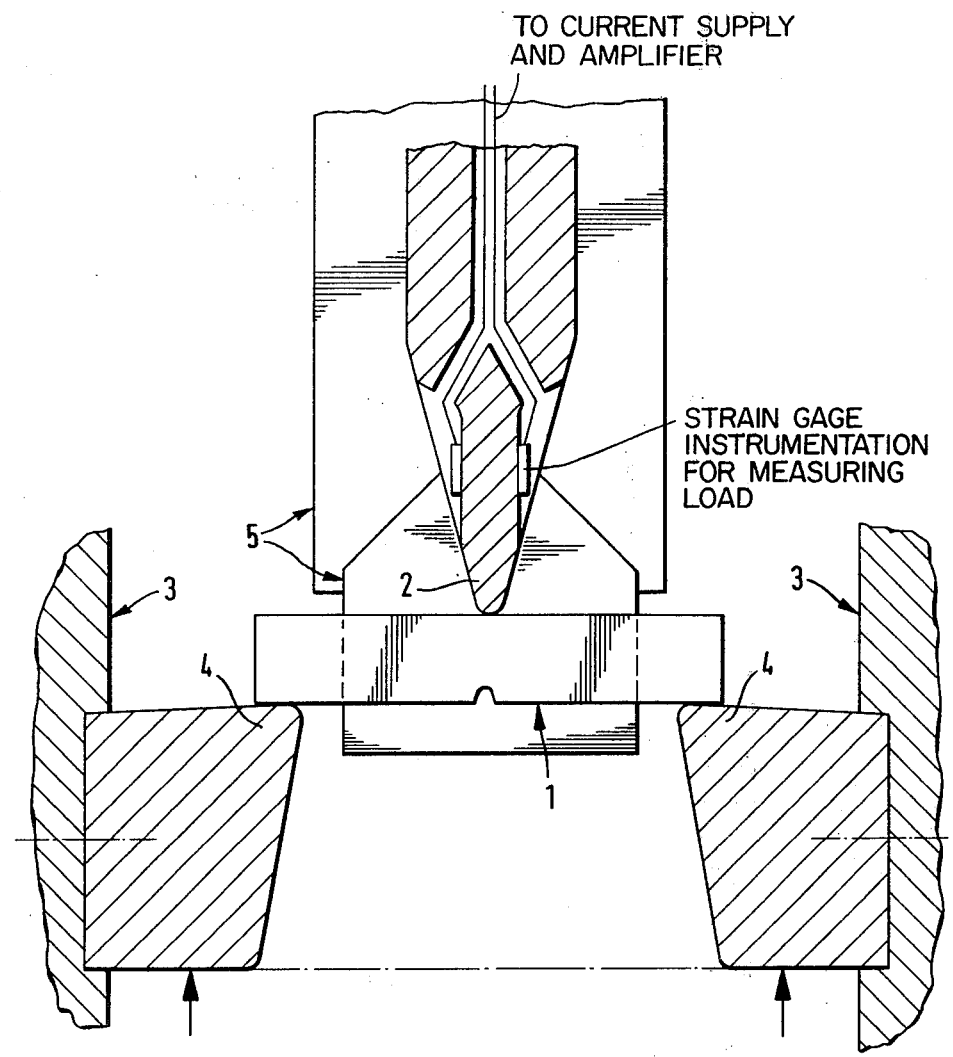
FIG. 5 illustrates a horizontal section along line A—A of the aforesaid apparatus.

FIG. 1 and FIG. 2 are described in the Background of the Invention because they present the state of the art. The apparatus according to the present invention is seen in FIGS. 3 to 5. In the apparatus a hammer 3 has been attached to a bar 7, which has been pivoted into a frame 6. The hammer and the bar form a pendulum, which is able to swing around the pivot 8 from the starting position 3a to a bottom position 3b. Other details, such as means for keeping the hammer in the upper position, etc., have not been presented. The stationary specimen 1 to be tested is bent round a stationary tup 2, which has been equipped with means for measuring the force which is acting on the specimen 1 during the impact. When the hammer swings down, two spaced-apart hitting edges 4 of the hammer 3 simultaneously hit both ends of the specimen 1. The specimen is supported by a plate 5 and is therefore free to deform when hit in the bending plane A—A.

What is claimed is:
1. A method for testing impact toughness of a bend specimen having a notch or similar in a middle portion thereof, which comprises:
(a) stationarily supporting said specimen in a middle area thereof by said specimen being placed symmetrically in contact against a stationary tup and at the opposite side of the specimen in relation to the notch therein;
(b) hitting the specimen at the notched side simultaneously at two end points positioned on each side of the middle area, so as to bend the specimen around the stationary tup; and
(c) measuring the force exerted by the hit specimen against said tup.
2. A method according to claim 1, wherein the specimen is supported in a horizontal plane with the notch being essentially vertical and the support force against middle area of the specimen is directed essentially horizontally, and the hitting movement and force at the moment of hitting being also essentially horizontal but in the opposite direction.
3. A method according to claim 2, wherein the specimen is centrally supported against said tup along a vertical line lying in the same plane normal to the specimen as said notch.
4. A method according to claim 1, wherein the bending force exerted on said specimen at the supported middle area of the specimen is measured by the force exerted horizontally against the stationary tup.
5. The method according to claim 1, wherein the bend specimen is hit by a swinging pendulum hammer mounted for pivotal movement and which hits the specimen at high velocity and bends the specimen against said stationary tup.
6. An apparatus for testing impact toughness of a bend specimen having a notch or similar in a middle portion thereof, said apparatus comprising:
(a) a frame;
(b) a stationary supporting member positioned at the lower part of the frame and extending in a horizontal direction and adapted to receive and support the bend specimen thereon;
(c) a supporting tup constituting a rigid part of said frame and positioned immediately above said support member so as to contact the bend specimen essentially at the middle part thereof, when the specimen is positioned on the supporting member, said supporting tup is provided with force measuring means, and
(d) a movable hammer, said hammer being attached to a bar which is pivotably connected to said frame, and having two hitting edges spaced apart from each other and being mounted for such pivotal movement in relation to said supporting tup that said hitting edges can hit simultaneously the supported bend specimen at each side of the middle portion thereof.
7. An apparatus according to claim 6, wherein the movable hammer is of pendulum type and is pivoted in one end at an upper portion of the frame, the specimen being supported in a position essentially vertically beneath said upper portion.

8. An apparatus according to claim 6, wherein the support tup is shaped so as to contact the bend specimen along a vertical line lying in the same normal plane of the specimen as said notch.

* * * * *